(12) United States Patent
Evans

(10) Patent No.: US 8,315,811 B1
(45) Date of Patent: Nov. 20, 2012

(54) METHOD FOR QUANTIFYING THE EXTENT OF HUMAN-INTRODUCED VARIABILITY IN MEDICAL TEST DATA

(76) Inventor: Mark Evans, Fort Lee, NJ (US)

( * ) Notice: Subject to any disclaimer, the term of this patent is extended or adjusted under 35 U.S.C. 154(b) by 531 days.

(21) Appl. No.: 12/551,027

(22) Filed: Aug. 31, 2009

Related U.S. Application Data

(60) Provisional application No. 61/232,178, filed on Aug. 7, 2009.

(51) Int. Cl.
*G01N 33/50* (2006.01)
*G01N 33/48* (2006.01)
(52) U.S. Cl. ............................................ 702/19; 702/20
(58) Field of Classification Search ........................ None
See application file for complete search history.

(56) References Cited

U.S. PATENT DOCUMENTS
2004/0106875 A1    6/2004    Menzie et al.

FOREIGN PATENT DOCUMENTS
| KR | 1020020005888 | 1/2002 |
| WO | 9427490 | 12/1994 |
| WO | 2008079305 | 7/2008 |

*Primary Examiner* — Jason Sims
(74) *Attorney, Agent, or Firm* — Dickinson Wright PLLC

(57) ABSTRACT

A method for quantifying the extent of human-introduced variability in medical test data relative to one or more standards for comparable medical tests, the method comprising the following steps: providing user medical test data; comparing the user medical test data against one or more standards for comparable medical tests to determine the extent of deviation of the user medical test data from the one or more standards; and generating a variability-value corresponding to the maximum absolute percentage deviation of the user medical test data from the one or more standards over a predefined operating range of values for the one or more standards.

27 Claims, 3 Drawing Sheets

METHOD FOR QUANTIFYING THE EXTENT OF HUMAN-INTRODUCED VARIABILITY IN MEDICAL TEST DATA

RELATED APPLICATIONS

This application claims the benefit of priority from U.S. provisional application Ser. No. 61/232,178, filed Aug. 7, 2009.

FIELD OF THE INVENTION

The invention pertains to a method for quantifying the extent of human-introduced variability in medical test data (laboratory and/or clinical).

BACKGROUND

Virtually all medical test data are subject to variability and bias introduced by the human clinicians responsible for generating these data. Exemplary of this heretofore unsolved problem are medical test data generated in connection with fetal screenings for the risk of birth defects.

First-trimester (usually between 11 and 13 weeks of the pregnancy) screenings are often performed to test for risk of Down syndrome, trisomy 18, and elevated risk of other chromosomal defects, congenital heart disease, and other genetic and congenital disorders. These screenings generally comprise a blood serum analysis component and an ultrasound component. The blood analysis, conducted by a laboratory, measures maternal blood levels of several analytes; commonly, free-beta human chorionic gonadotropin (hCG) and pregnancy-associated protein A (PAPP-A). For instance, levels of PAPP-A tend to be decreased, and hCG increased, with Down syndrome. The ultrasound component, conducted by a physician or technician, involves measuring nuchal translucency ("NT"), which is the thickness of the fluid space in the tissue at the back of the fetus's neck. Increased NT is generally associated with Down syndrome, other chromosomal abnormalities, and several other genetic and congenital disorders.

The risk for Down syndrome and other defects is calculated based upon the combined results of the blood serum analysis and ultrasound components. Relative to each of the NT and blood serum components of the screening, there is a certain likelihood ratio ("LR") associated with the results. The LR is an historically-derived ratio representing the number of healthy to abnormal fetuses for a given result. With the NT measurement, for instance, there is, for a given fetal crown-rump length ("CRL"), an LR for each NT measurement within that CRL. The LR is multiplied by an a priori, or background, risk factor based on maternal age (the risk of birth defects is documented to increase with the age of the mother) and gestational age to yield an adjusted risk specific to the patient ("patient-adjusted risk"). Again with respect to the NT measurement specifically, it is generally the case that the smaller the NT measurement, the lower the adjusted risk. Conversely, larger NT measurements generally equate to a higher adjusted risk.

In laboratory medicine it is routine to constantly quality control the data. Clinicians understand that every time they send a blood test to the lab, the lab is on a regular basis double-checking their results against known controls. This has not been the case with NT measurements, which in the United States are generally uncertified or controlled. Unfortunately, this translates into patients being falsely reassured that their pregnancies are normal when they may actually be having a baby with Down syndrome and/or one or more other serious birth defects or, conversely, being falsely warned that the pregnancy is abnormal when, in fact, this is not the case.

As the use of NT screening has increased, human-introduced variability has had a profound negative impact upon overall performance, creating considerable controversy in how to account for biases in these measurements, e.g. individual vs. national curves.

What is more, these differences in measurements are costly. It has been shown that a 3% improvement in NT screening performance in the United States could produce an annual cost savings of $100 million for combined first trimester screening.

To address this problem, the Fetal Medicine Foundation ("FMF") established a training process requiring a written test, submission of images for grading, and continuing, periodic recertification. This has been adopted without much opposition in much of the world outside of the United States. In this country, the Society for Maternal Fetal Medicine set up the Nuchal Translucency Quality Review program (NTQR) to oversee training and review of U.S. physicians. NTQR provides an internet-based program for educating, testing proficiency, and reviewing the quality of NT screening professionals. NTQR monitors the quality of participating members, with members whose quality is found to be deficient as compared to the prevailing standard being identified for remediation. Nevertheless, while remediation may improve future NT screening results, the problem of patients being provided presently false data in respect of those screenings known to be of deficient quality remains unresolved.

SUMMARY

The invention pertains to a method for quantifying the extent of human-introduced variability in medical test data relative to one or more standards for comparable medical tests. According to a first embodiment, the method comprises the following steps: Providing user medical test data; comparing the user medical test data against one or more standards for comparable medical tests to determine the extent of deviation of the user medical test data from the one or more standards; and generating a variability-value corresponding to the maximum absolute percentage deviation of the user medical test data from the one or more standards over a predefined operating range of values for the one or more standards.

Per one feature thereof, the invention further comprises the step of correcting the user medical test data by the extent of deviation from the one or more standards determined for the user medical test data.

The user medical test data may, per one aspect of the invention, comprise one or more of fetal nuchal translucency measurements, maternal serum PAPP-A measurements, and free β-hCG measurements. The user fetal nuchal translucency measurements, maternal serum PAPP-A measurements, and free β-hCG measurements may each be expressed as a multiple of a gestation-specific median value. Further according to this aspect of the inventive method, the step of comparing the user fetal nuchal translucency measurements against one or more standards comprises comparing the distribution of the user fetal nuchal translucency measurements against fetal nuchal translucency measurements, expressed as multiples of a gestation-specific median value, representing average fetal nuchal translucency measurements for a statistically significant population, to determine the percentage deviation therefrom represented by the user fetal nuchal translucency measurements, while the step of generating a variability-value comprises determining the likelihood ratio over a predefined operating range for average fetal nuchal translucency measurements, determining the likelihood ratio, over the predefined operating range, for the user fetal nuchal translucency measurements, and identifying the maximum deviation, expressed as an absolute value, of the likelihood ratio for the user fetal nuchal translucency measurements from the likelihood ratio for average fetal nuchal translucency measurements. Still further according to this embodiment, the step of comparing the user maternal serum PAPP-A and free β-hCG measurements against one or more standards comprises comparing the distribution of the one or more user maternal serum PAPP-A and free β-hCG measurements against maternal serum PAPP-A and free β-hCG measurements, expressed as multiples of a gestation-specific median value, representing average maternal serum PAPP-A and free β-hCG measurements for a statistically significant population, to determine the percentage deviation therefrom represented by the user maternal serum PAPP-A and free β-hCG measurements, while the step of generating a variability-value comprises determining the likelihood ratio over a predefined operating range for average maternal serum PAPP-A and free β-hCG measurements, determining the likelihood ratio, over the predefined operating range, for the user's maternal serum PAPP-A and free β-hCG measurements, and identifying the maximum deviation, expressed as an absolute value, of the likelihood ratio for the user maternal serum PAPP-A and free β-hCG measurements from the likelihood ratio for average maternal serum PAPP-A and free β-hCG measurements.

The inventive method may be implemented through a subscription system which, according to one embodiment, comprises the following steps: Providing at least one database for maintaining medical test data submitted by one or more subscribers; comparing each subscriber's medical test data against one or more standards for comparable medical tests to determine the extent of deviation of each subscriber's medical test data from the one or more standards; generating a subscriber-specific variability-value corresponding to the maximum absolute percentage deviation of the subscriber's medical test data from the one or more standards over a predefined operating range of values for the one or more standards; and providing the subscriber-specific variability-value to at least the subscriber.

According to one feature, the method further comprises the step of correcting each subscriber's medical test data by the extent of deviation from the one or more standards determined for the subscriber's medical test data.

Per another feature, the one or more standards are based upon the average medical test results derived from the at least one database for maintaining medical test data submitted by the one or more subscribers.

BRIEF DESCRIPTION OF THE DRAWINGS

The present invention will be appreciated from the following description and accompanying drawings, of which.

WRITTEN DESCRIPTION

As required, detailed embodiments of the present invention are disclosed herein; however, it is to be understood that the disclosed embodiments are merely exemplary of the invention that may be embodied in various and alternative forms. The accompanying drawings are not necessarily to scale, and some features may be exaggerated or minimized to show details of particular components. Therefore, specific structural and functional details disclosed herein are not to be interpreted as limiting, but merely as a representative basis for teaching one skilled in the art to variously employ the present invention.

Referring then to the drawings, the invention pertains to a method for quantifying the extent of human-introduced variability in medical test data (laboratory and/or clinical). More particularly, and with reference being had to FIG. 1, the inventive method comprises, according to an exemplary embodiment, the steps of providing a user's (e.g., a clinician, laboratory technician, etc.) medical test data 10, comparing a user's medical test data against one or more standards for comparable medical tests to determine the extent of variability of the user's medical test data from the one or more standards 11, and generating a variability-value, also referred to herein as a performance adjusted risk ("PAR"), corresponding to the maximum absolute percentage deviation of the user's submitted medical test data from the one or more standards 12.

Figure 1:
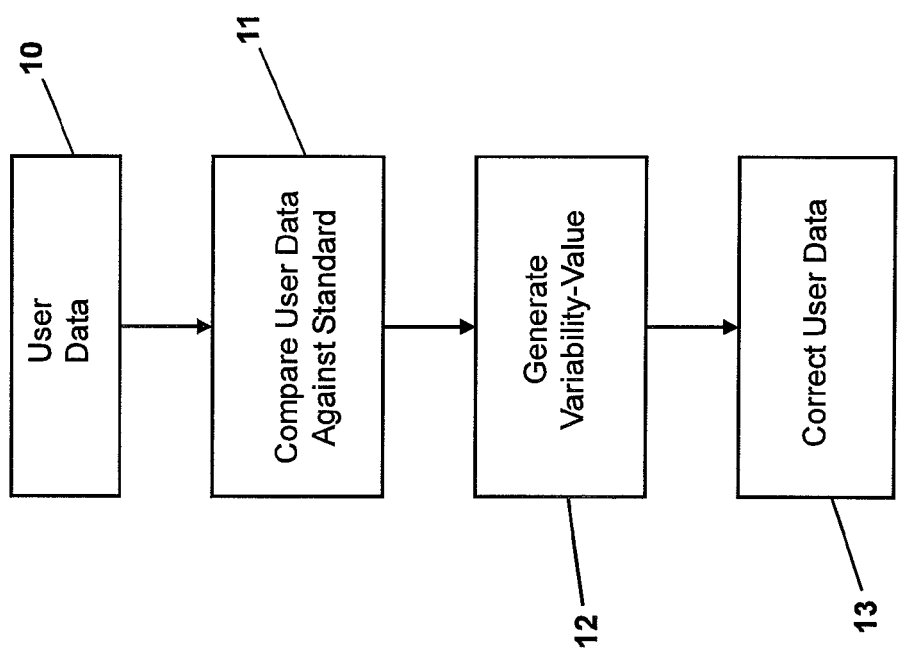
FIG. 1 is a flow-chart depicting the inventive method according to an embodiment thereof.

As further shown in FIG. 1, the inventive method may also, optionally comprehend the step 13 of correcting the user's medical test data by the extent of variability from the one or more standards determined for the user's medical test data. That step, if included, may be performed either before or after the variability, or PAR, value is generated in step 12.

For those users whose prevailing variability, or PAR, value is below average, for instance, one or more of the components measured in a medical test may be appropriately weighted to permit such users' test data to be used in practice to advise patients without exposing those patients to the users' relatively inferior performance. In example, a user who constantly over-measures NT—and thus has a PAR value that is higher than the average—would have the input of those NT measurements be a smaller component (in proportion to that user's relative deviation from the expected distribution of measurements employed as the standard) of the combined risk computed to be given to the patient. Conversely, a user whose NT measurements are closer to the average would have the input of those measurements be a proportionally larger component of the combined risk computed to be given to the patient.

Thus, the invention allows for the prioritization of high quality data over poorer quality data.

The PAR value may, as explained below, be provided to the user and or others to also serve as an indicator of the user's performance relative to others in generating the medical test data and, relatedly, as a means of incentivizing the user to improve their performance in generating such medical test data.

While applicable in connection with first trimester screening for Down syndrome and other defects of the type described above, in connection with which screening the exemplary embodiments of the invention are hereafter described, it will be appreciated from the disclosure that the invention may be applied also to other medical tests where the introduction of variability is possible.

Using the first-trimester Down syndrome screening described above as only an exemplary environment for employment thereof, the steps of comparing each user's medical test data against one or more standards for comparable medical tests and, optionally, of correcting that medical test data are described below.

As noted, ultrasound measurement of fetal NT is conventionally employed at 11-13 weeks gestation to determine the risk of Down syndrome in the fetus. Since NT changes with gestation, these measurements are typically expressed as multiples of gestation-specific normal medians ("MoMs"). Down syndrome risk is estimated by applying to the pre-test risk (based on, for instance, standard maternal age charts) a LR derived from the overlapping log-Gaussian frequency distributions of NT MoM values in Down syndrome and unaffected pregnancies. There are presently available historically-generated distribution data establishing the expected distribution of NT measurements for any given CRL measurement for both Down syndrome and unaffected pregnancies. These distribution data may provide the standard employed to evaluate a user's NT measurement data. Within this context, generating a user-specific variability-value, or PAR, corresponding to the maximum absolute percentage deviation of a user's actual LR from a predetermined LR from over a predefined range of MoMs more particularly comprises the steps of: Comparing the distribution of one or more user fetal NT measurements against fetal NT measurements, expressed as multiples of a gestation-specific median value, representing average fetal NT measurements for a statistically significant population, to determine the percentage deviation therefrom represented by the one or more user fetal NT measurements, and thereafter determining a variability-value by determining the LR over a predefined operating range for average fetal NT measurements, determining the LR, over the predefined operating range, for the one or more user fetal NT measurements, and identifying the maximum deviation, expressed as an absolute value, of the LR for the one or more user fetal NT measurements from the LR for average fetal NT measurements.

Still more particularly, the foregoing methodology is, per the exemplary embodiment, characterized by "actual" and "comparative" elements. The "comparative" element comprises LRs representing average human scanning performance in NT measurements for Down syndrome and unaffected pregnancies, while the "actual" element comprises the LRs for the user's NT measurements being quantified.

The "comparative" element is characterized by the following formula:

$$LR = SD_{UN}/SD_{DS} * \exp(-0.5(Z_{DS}^2 - Z_{UN}^2))$$

Wherein, $Z_{DS} = (\log_{10}\text{MoM} - \log_{10}M_{DS})/SD_{DS}$ and $Z_{UN} = (\log_{10}\text{MoM} - \log_{10}M_{UN})/SD_{UN}$. In the foregoing, $M_{DS}$ is the mean LR in Down syndrome cases; $M_{UN}$ is the mean LR in cases unaffected by Down syndrome; $SD_{DS}$ is the mean LR in Down syndrome cases; and $SD_{UN}$ is the mean LR in cases unaffected by Down syndrome.

The "actual" aspect of the first element is characterized by essentially the same formula:

$$LR = SD1_{UN}/SD1_{DS} * \exp(-0.5(Z1_{DS}^2 - Z1_{UN}^2))$$

The means and standard deviations may be derived from the published literature, representing average scanning performance. As will be understood by those skilled in the art, the relevant parameters may alter with the time of gestation.

As explained further below, the invention according to one embodiment contemplates implementation through a subscription service or the like. Per this embodiment, it is further contemplated that the standard data against which the user medical test data are compared may be augmented by, or substituted with, the data submitted by users of such a service. In other words, the medical test data provided by the users of such a service may comprise part of, or the entire, population of standard data against which later user-submitted medical test data are compared.

The following are hypothetical exemplary applications of the foregoing aspect of the invention.

Hypothetical Example 1

At 12 weeks gestation, the MoM for Down syndrome pregnancies is 2.10, the MoM for unaffected pregnancies is 1.00, the standard deviation of $\log_{10}\text{MoM}$ is 0.24 for Down syndrome pregnancies, and the standard deviation for unaffected pregnancies is 0.12.

In this example, an ultrasound operator is found to have a less accurate distribution than this, measuring 10% higher than the average performance. In that case, the extent of deviation of the actual LR from the comparative. LR is estimated by statistical modeling with the means increased by 10%. Over the effective operating range (0.6-1.7 MoM) the maximum deviation is 200%. This is the user-specific variability, or PAR, value.

Hypothetical Example 2

As in Hypothetical Example 1, except that the operator is found to measure 10% below the average. In this case the user-specific variability, or PAR, value over the effective operating range (0.6-1.7 MoM) will be 240%.

Hypothetical Example 3

Unlike in Hypothetical Example 1, the operator is found to measure accurately but with lower precision by measuring with a standard deviation 0.01 wider than average. In this case, the user-specific variability, or PAR, value will be 120% over the effective operating range (0.6-1.7 MoM).

Determination of the user-specific variability, or PAR, value may be extended to myriad user test data. For instance (and continuing with the exemplary embodiment of the invention), it is contemplated that a variability, or PAR, value may be generated for blood serum analysis test data as well as for NT test data such as noted above. As previously, this application of the inventive method is characterized by "actual" and "comparative" elements; where the "comparative" element comprises LRs representing average human performance in blood serum analysis for Down syndrome and unaffected pregnancies, and "actual" elements comprises LRs for the user's blood serum analysis being quantified.

The comparative element is, more particularly, characterized by the following formula:

$$LR = \sqrt{|COV_{UN}|}/\sqrt{|COV_{DS}|} \exp(-0.5(D_{DS} - D_{UN}))$$

Wherein, $COV_{UN}$ and $COV_{DS}$ are covariance matrices for unaffected and Down syndrome pregnancies, respectively, derived from standard deviations and correlation coefficients between each marker pair in the serum analysis; $D_{DS} = (\log_{10}\text{MoM} - M)^T * COV^{-1} * (\log_{10}\text{MoM} - M)$ and $D_{UN} = (\log_{10}\text{MoM} - M)^T * COV^{-1} * (\log_{10}\text{MoM} - M)$. In the foregoing formulae, $\log_{10}\text{MoM}$ is the vector of $\log_{10}\text{MoMs}$; and M is the vector of Ms.

As those skilled in the art will understand, covariance is a measure of how much two variables change together. If two variables tend to vary together, up or down, then the covariance between the two variables will be positive. On the other hand, if one of them tends to be above its expected value when the other variable is below its expected value, then the covariance between the two variables will be negative. The covariance matrix, or COV, is a matrix of the covariances between elements of a random vector.

The following are hypothetical, exemplary applications of the foregoing aspect of the invention.

Hypothetical Example 4

As noted above, multiple maternal serum markers are also evaluated, typically at 14-20 weeks gestation, to determine the risk of Down syndrome. Since all serum marker levels change with gestation, the results of these evaluations are also expressed as MoMs. As in Example 1, Down syndrome risk is estimated using an LR from log-Gaussian distributions in this multi-variate. In addition to the individual marker means and standard deviations, the system of the invention used to determine LR uses correlation coefficients between each marker pair. All parameters are derived from the published literature, representing average analytical performance.

In this example, a laboratory carrying out the Quad test (comprised of the four markers: AFP, $uE_3$, hCG and inhibin) is found to have inaccurate hCG and AFP analysis, measuring them 10% higher and lower, respectively, than the average. In that case, the extent of deviation of the actual LR from that generated by the system can be estimated by statistical modeling with the means increased and reduced, respectively, by 10%. Over the effective operating range of all four markers (0.6-1.7 MoM for hCG and inhibin; 0.5-1.5 MoM for AFP and $uE_3$) the maximum deviation is 150%. This is the user-specific variability, or PAR, value.

Hypothetical Example 5

Ultrasound NT together with maternal serum PAPP-A and free β-hCG (so-called "Combined test") is conventionally used at 11-13 weeks gestation to determine the risk of Down syndrome. As in Example 4, above, Down syndrome risk is estimated using an LR from multi-variate, log-Gaussian distributions. All parameters are derived from the published literature, representing average ultrasound and analytical performance.

In this example, a laboratory carrying out the Combined test is found to have inaccurate free β-hCG analysis, measuring 10% higher than average, and an ultrasound operator sending samples to the laboratory is found to measure NT 10% higher than the average performance. Over the effective operating range of the three markers (0.6-1.7 MoM for NT and free β-hCG; 0.5-1.5 MoM for PAPP-A) the maximum deviation is 240%. This is the user-specific variability, or PAR, value.

The inventive method may, as noted, optionally include the step of correcting the user medical test data by the extent of variability from the one or more standards determined for the user's medical test data. For those users whose prevailing variability, or PAR, value is below average, for instance, one or more of the measured components in the foregoing formulas may be appropriately weighted to permit such users' test data to be used in practice to advise patients without exposing those patients to the users' relatively inferior performance.

Continuing with the examples cited above, for instance, a user's NT measurement(s) may show a deviation (as an overestimation of NT length or an underestimation of NT length) by a certain percentage (e.g., 20%) from the expected distribution of NT measurements according to the data employed as the reference standard. According to this example, therefore, the user's NT measurement would be adjusted by 20%, either upwardly (if the user's data distribution reflects an overall underestimation of NT length) or downwardly (if the user's data distribution reflects an overall overestimation of NT length).

Of course, it is contemplated the corrective adjustment applied to a user's medical test data pursuant to the present invention can be according to any desired scale or standard, the only requirement being that, for the medical test data in question, the scale or standard relatively weight the relevant component(s) of each user's medical test data by the extent of variability in the component(s) from the one or more standards determined for the user's medical test data such that those users whose extent of variability is further from the one or more standards is discounted so as to be a smaller component in any computation or analysis (such as, for instance, the LR determinations described above) than those users whose extent of variability is closer to the one or more standards. Thus, for instance, it is contemplated that such a scale or standard may accord full weight (e.g., a multiplier of 1 or, alternatively, a discount value of 0) to a user's medical test data that comports with the one or more standards against which the extent of variability is determined, while according relatively less weight to users' medical test data pursuant to the extent of variability from that benchmark. Optionally, it is contemplated that user medical test data that comports with the one or more standards against which the extent of variability is determined may be favorably weighted (e.g., a multiplier of greater than 1) to reflect an above-average level of performance in generating the medical test data.

It is further contemplated that the scale or standard may correlate more directly with the PAR values determined according to the invention (as opposed to the PAR values being, for instance, merely reflective of each user's relative performance in generating the medical test data). For example, it is contemplated that the corrective adjustment may be a scale according to which each integer of the absolute PAR number relates to a corresponding weight applied to the relevant component(s) of the medical test data.

Though not absolutely necessary, it is desirable that a user's extent of deviation from the one or more standards be evaluated on a regular basis so that the step of correcting the user's medical test data will more accurately reflect the user's prevailing performance. Ideally, this evaluation is performed each time a user submits medical test data (such as via the system described below), so that any corrective adjustment will reflect the user's deviation for those particular test data.

As noted, the method of the invention may be implemented through an enrollment or subscription system, wherein the users are subscribers. Such subscribers may, for instance, be individual clinicians or technicians and/or groups of clinicians or technicians, such as, for instance, a laboratory or clinic.

Figure 2:
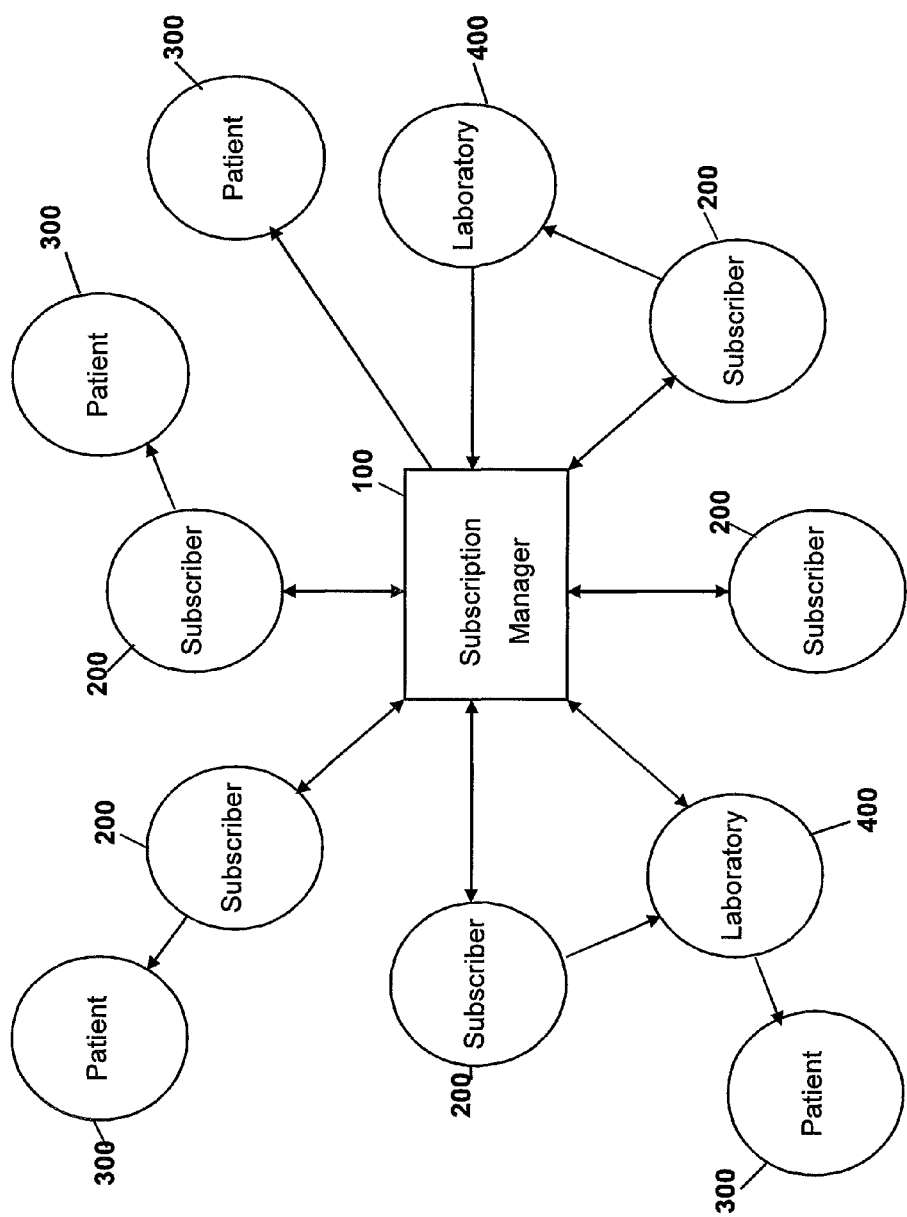
FIG. 2 is a diagrammatic depiction of an exemplary architecture for a system comprising the invention.

According to this embodiment of the invention, there may be provided a subscription manager 100 responsible for receiving and maintaining test data, such as NT measurements and associated information (including, for example, one or more of the LR, adjusted risk, CRL, maternal age, gestational age, etc.) from each of a plurality of subscribers 200, and communicating information, including (optionally) information about how each subscriber's test data are to be adjusted, back to the subscribers 200 and/or one or more non-subscribing third parties such as the patient 300 or laboratory 400. These subscribers 200 may be positioned in the same or disparate locations and may comprise one or more parties involved in performing the medical test(s) in question (e.g., NT measurement and/or blood serum analysis) including, for instance, the physician or clinician, the laboratory, technician, etc. (FIG. 2.)

The system manager 100 will further maintain, or have access to, the one or more standards against which subscriber data is compared.

Each subscriber's submitted data are maintained in one or more databases and compared to the standard or standards maintained in the same or different database or databases, or accessible by the system manager via another source, to develop the variability, or PAR, value.

It will be appreciated that, over time, the accumulation of each subscriber's submitted data will lead to the development of a large subscriber-specific database—which may be separate from or included as a subset of data in the database of standard or standards—that facilitates the more accurate assessment of the subscriber's performance in developing the submitted data as compared to the standard or standards. It is contemplated that, in one embodiment, the standard data against which the subscriber medical test data are compared may be augmented by, or substituted with, the data submitted by the subscribers' own medical test data. Thus, for example, the standard for NT measurements may be derived from the average NT measurement performance of all subscribers' submitted NT measurement data.

Continuing with the first-trimester screening of the exemplary embodiment, the system manager 100 would update the subscriber's database 130 with the latest subscriber medical test data 120 (whether submitted directly by the subscriber or another party), compare 140 the subscriber's medical test data against one or more standards for comparable medical tests to determine the extent of variability of the subscriber's medical test data from the one or more standards, and generate a variability-value corresponding to the maximum absolute percentage deviation of the subscriber's medical test data from the one or more standards, all as described above (FIG. 3).

The system manager may optionally (also shown at 140 in FIG. 3) correct the subscriber's medical test data by the determined extent of variability, such as in the manner discussed above.

Receipt of the data may be according to known means, including, for instance, via the internet. The system manager 100 may comprise a network server or servers to which the data may be directly submitted from the subscribers 200 or one or more non-subscribing third parties involved in the screening, such as, for example, a third party laboratory 400 participating in the ultrasound measurements and/or the blood analysis. Exemplary paths for the submission of data to the system manager are identified by directional arrows pointing toward the system manager 100 in FIG. 2.

Enrollment or subscription may involve an initial, and even an ongoing, credentialing process by which each subscriber is required to establish a benchmark. As desired, the credentialing process may include an educational component to develop the subscriber's competency in the development of data of the type submitted to the system manager. In the exemplary embodiment, for instance, where the data comprise NT measurements, such an educational component may include training the subscriber or, where the subscriber is a business, the subscriber's employees in the operation of ultrasound apparatus (e.g., hardware and software) to develop competency in taking NT and associated (e.g., CRL) measurements.

Whether or not such a benchmark is established, it is further contemplated that each new subscriber's data may be adjusted by a predetermined value (which may be the same value for every new subscriber) given the absence in the system manager's database of historical data for that subscriber. This value may be neutral (i.e., 0) or a value giving a predetermined discount to the new subscriber's data. The predetermined value may be based, for instance, on historical averages established by the system manager 10 or by a third party, and may, for example, reflect an adjustment value appropriate to a median of novice medical test performers. Using the exemplary NT measurement test of the embodiment described herein, the initial adjustment, or PAR, value provided to a subscriber may comprehend the average deviation from a standard of NT measurements for ultrasound operators having no practical experience in taking NT measurements.

Alternatively, enrollment accompanied by credentialing may, as noted, be employed to assign a new subscriber a value related to the credentialing process. For instance, where credentialing comprises the new subscriber's submission of data for mock (i.e., for evaluation purposes only) screenings, such as NT and related measurements taken from mock or exemplary sonograms, the deviation of these data from the standard or standards may provide the basis for providing the new subscriber with a value for adjusting their data prospectively.

Figure 3:
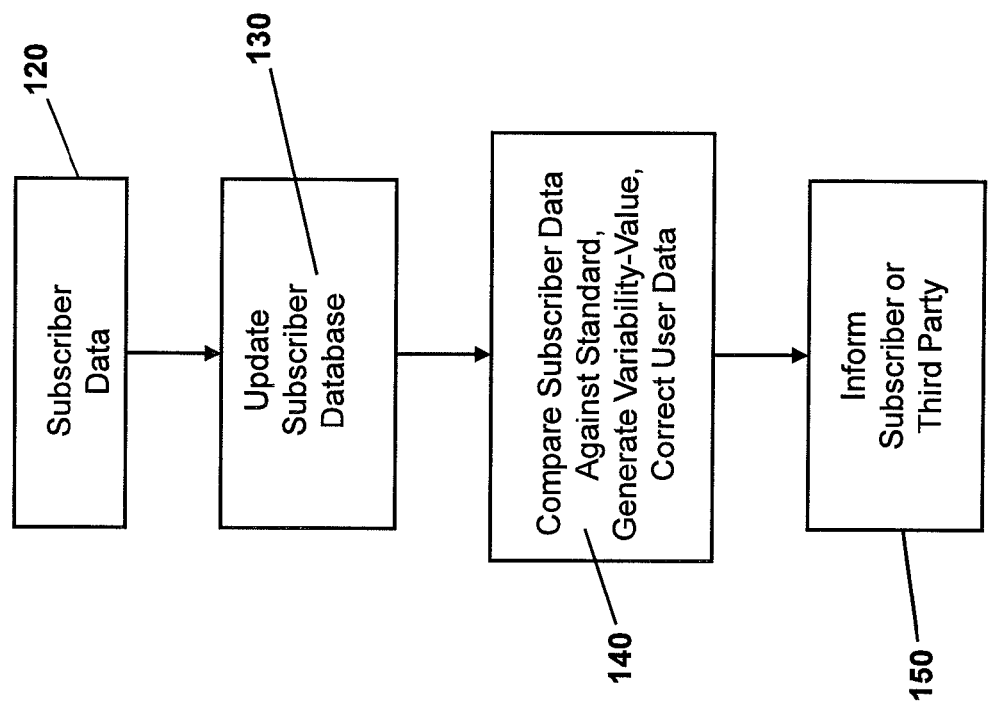
FIG. 3 is a flow-chart depicting the operation of the system of the embodiment of FIG. 2.

Still referring to FIGS. 2 and 3, the prevailing variability, or PAR, value determined by the system manager may be returned to the subscriber 150 and/or provided to another party, including another subscriber, such as a laboratory or even the patient.

Alternatively, or in addition, any one or more of the foregoing parties may be provided with the test result (e.g., the patient-adjusted risk), or another component thereof (e.g., the LR) by the system manager. Accordingly, the system manager may perform all or any part of the screening or other test and, depending upon the system manager's contribution thereto, that contribution may be forwarded to the appropriate party or parties. Thus, it is contemplated that the system manager may receive and compile all relevant data and generate a test result for forwarding to the patient, to a laboratory for dissemination to the patient, or to a clinician or technician for dissemination to a patient. It is also contemplated that the system manager may receive only the subscriber's data, which data may then be returned (discounted with the adjustment value or accompanied by the adjustment value for computation by the recipient) to the subscriber for generation of the test result, or to another party (e.g., a laboratory) for combination of such data with additional data (such as, for instance, biochemical data). It is also contemplated that such recipient may itself subsequently provide that and other data to another party, for instance, back to the subscriber, to a clinician or technician, etc., for distribution to the patient, or directly on to the patient. Exemplary paths for the transmission of these data to from the system manager and on to the subscriber and/or one or more non-subscribing third parties are identified by directional arrows leading to the subscribers 200 and/or one or more non-subscribing third parties 300, 400 in FIG. 2.

Even where the prevailing variability, or PAR, value is not provided to the subscriber or other party, the present system contemplates that such party may be provided feedback on the extent of deviation from the norm of a subscriber's results so they can undertake corrective measures. To this end, it is further contemplated that such corrective measures, including follow-on training, certification, or the like, may be provided, or the provision of such follow-on training, certification or the like facilitated by the system manager.

While such feedback 150 may be provided as regularly as desired, it is contemplated that each subscriber's prevailing variability, or PAR, value and any other information communicated from the system manager may be provided as often as test data are provided to the system manager, or even more frequently. In this fashion, each subscriber will, with each update to the subscriber database, be provided feedback, in the form of at least the then prevailing PAR value, representative of the subscriber's present deviation from the standard or standards. In this fashion, the subscriber will be provided a sense of whether or not, and relatively how much, further training may be required of him/her/it to develop test data consistent with the standard or standards.

It is also contemplated that each subscriber may have ready access, for instance via the internet, to at least their respective adjustment values and/or other information (e.g., certification or testing results, etc.) generated by the subscription manager.

It will be appreciated from the foregoing disclosure that the present invention analyzes individual user data distributions and assigns a "handicap"—the PAR value—with user's having data distributions that significantly deviate from national or other established expectations being given a higher PAR value than those whose data distributions are closer to established expectations. Furthermore, the greater the PAR value, the lower the contribution of that parameter value into the algorithmic determination of risk.

In example, it has been found in a study of 7,372 women having a median age of 36 at delivery and NT measurements performed at a single center, that by employing the present invention to weight the NT measurements according to their deviation from a standard, and using those weighted NT measurements to determine LRs for the study population, the Trisomy 21 detection rate increased from 67% to 70%, while the detection rate for other aneuploidies increased from 70% to 77%.

By adjusting for individual cases and by informing providers of their PAR value and its relationship to the PAR values of others, the present invention gives incentives to improve performance, thereby striking a balance between the conventional practices of individual medians, which lower performance and give no incentives to improve, and national medians, which set a higher standard but allow poor performers to generate inaccurate risks.

The foregoing description of the exemplary embodiment of the invention has been presented for purposes of illustration and description. It is not intended to be exhaustive or to limit the invention to the precise form disclosed, and modifications and variations are possible in light of the above teachings or may be acquired from practice of the innovation. The embodiments are shown and described in order to explain the principles of the innovation and its practical application to enable one skilled in the art to utilize the innovation in various embodiments and with various modifications as are suited to the particular use contemplated. Although only a few embodiments of the present innovations have been described in detail in this disclosure, those skilled in the art who review this disclosure will readily appreciate that many modifications are possible without materially departing from the novel teachings and advantages of the subject matter recited. Accordingly, all such modifications are intended to be included within the scope of the present innovations. Other substitutions, modifications, changes and omissions may be made in the design, operating conditions and arrangement of the exemplary embodiments without departing from the spirit of the present innovations.

The invention in which an exclusive property or privilege is claimed is defined as follows:

1. A method for quantifying the extent of human-introduced variability in medical test data relative to one or more standards for comparable medical tests, the method comprising the following steps:

providing user medical test data stored in a computer-readable storage medium;

comparing the user medical test data against one or more standards for comparable medical tests and determining the extent of deviation of the user medical test data from the one or more standards; and generating a variability-value corresponding to the maximum absolute percentage deviation of the user medical test data from the one or more standards over a predefined operating range of values for the one or more standards;

wherein the user medical test data comprise fetal nuchal translucency measurements;

wherein the user fetal nuchal translucency measurements are expressed as a multiple of a gestation-specific median value;

wherein the step of comparing the user fetal nuchal translucency measurements against the one or more standards comprises comparing the distribution of the user fetal nuchal translucency measurements against fetal nuchal translucency measurements, expressed as multiples of a gestation-specific median value, representing average fetal nuchal translucency measurements for a statistically significant population, and determining the percentage deviation therefrom represented by the user fetal nuchal translucency measurements; and wherein the step of generating a variability-value comprises determining the likelihood ratio over a predefined operating range for the average fetal nuchal translucency measurements, determining the likelihood ratio, over the predefined operating range, for the user fetal nuchal translucency measurements, and identifying the maximum deviation, expressed as an absolute value, of the likelihood ratio for the user fetal nuchal translucency measurements from the likelihood ratio for the average fetal nuchal translucency measurements.

2. The method of claim 1, further comprising the step of correcting the user medical test data by the extent of deviation from the one or more standards determined for the user medical test data.

3. The method of claim 1, wherein:

the user medical test data further comprise maternal serum PAPP-A measurements;

the user maternal serum PAPP-A measurements are expressed as a multiple of a gestation-specific median value;

the step of comparing the user maternal serum PAPP-A measurements against the one or more standards comprises comparing the distribution of the user maternal serum PAPP-A measurements against maternal serum PAPP-A measurements, expressed as multiples of a gestation-specific median value, representing average maternal serum PAPP-A measurements for a statistically significant population, and determining the percentage deviation therefrom represented by the user's maternal serum PAPP-A measurements; and the step of generating a variability-value comprises determining the likelihood ratio over a predefined operating range for the average maternal serum PAPP-A measurements, determining the likelihood ratio, over the predefined operating range, for the user maternal serum PAPP-A measurements, and identifying the maximum deviation, expressed as an absolute value, of the likelihood ratio for the user's maternal serum PAPP-A measurements from the likelihood ratio for the average maternal serum PAPP-A measurements.

4. The method of claim 3, further comprising the step of correcting the user medical test data by the extent of deviation from the one or more standards determined for the user medical test data.

5. The method of claim 1, wherein:
the user medical test data further comprise free β-hCG measurements;
the user maternal serum free β-hCG measurements are expressed as a multiple of a gestation-specific median value;
the step of comparing the user free β-hCG measurements against the one or more standards comprises comparing the distribution of the free β-hCG measurements against free β-hCG measurements, expressed as multiples of a gestation-specific median value, representing average free β-hCG measurements for a statistically significant population, and determining the percentage deviation therefrom represented by the user free β-hCG measurements; and
the step of generating a variability-value comprises determining the likelihood ratio over a predefined operating range for the average free β-hCG measurements, determining the likelihood ratio, over the predefined operating range, for the user free β-hCG measurements, and identifying the maximum deviation, expressed as an absolute value, of the likelihood ratio for the user free β-hCG measurements from the likelihood ratio for the average free β-hCG measurements.

6. The method of claim 5, further comprising the step of correcting the user medical test data by the extent of deviation from the one or more standards determined for the user medical test data.

7. A method for quantifying the extent of human-introduced variability in medical test data relative to one or more standards for comparable medical tests, the method comprising the following steps:
providing user medical test data stored in a computer-readable storage medium;
comparing the user medical test data against one or more standards for comparable medical tests and determining the extent of deviation of the user medical test data from the one or more standards; and
generating a variability-value corresponding to the maximum absolute percentage deviation of the user medical test data from the one or more standards over a predefined operating range of values for the one or more standards;
wherein the user medical test data comprise maternal serum PAPP-A measurements;
wherein the user maternal serum PAPP-A measurements are expressed as a multiple of a gestation-specific median value;
wherein the step of comparing the user maternal serum PAPP-A measurements against the one or more standards comprises comparing the distribution of the user maternal serum PAPP-A measurements against maternal serum PAPP-A measurements, expressed as multiples of a gestation-specific median value, representing average maternal serum PAPP-A measurements for a statistically significant population, and determining the percentage deviation therefrom represented by the user maternal serum PAPP-A measurements; and
wherein the step of generating a variability-value comprises determining the likelihood ratio over a predefined operating range for the average maternal serum PAPP-A measurements, determining the likelihood ratio, over the predefined operating range, for the user maternal serum PAPP-A measurements, and identifying the maximum deviation, expressed as an absolute value, of the likelihood ratio for the user maternal serum PAPP-A measurements from the likelihood ratio for the average maternal serum PAPP-A measurements.

8. The method of claim 7, further comprising the step of correcting the user medical test data by the extent of deviation from the one or more standards determined for the user medical test data.

9. The method of claim 7, wherein:
the user medical test data further comprise fetal nuchal translucency measurements;
the user fetal nuchal translucency measurements are expressed as a multiple of a gestation-specific median value;
the step of comparing the user fetal nuchal translucency measurements against the one or more standards comprises comparing the distribution of the user fetal nuchal translucency measurements against fetal nuchal translucency measurements, expressed as multiples of a gestation-specific median value, representing average fetal nuchal translucency measurements for a statistically significant population, and determining the percentage deviation therefrom represented by the user fetal nuchal translucency measurements; and
the step of generating a variability-value comprises determining the likelihood ratio over a predefined operating range for the average fetal nuchal translucency measurements, determining the likelihood ratio, over the predefined operating range, for the user fetal nuchal translucency measurements, and identifying the maximum deviation, expressed as an absolute value, of the likelihood ratio for the user fetal nuchal translucency measurements from the likelihood ratio for the average fetal nuchal translucency measurements.

10. The method of claim 9, further comprising the step of correcting the user medical test data by the extent of deviation from the one or more standards determined for the user medical test data.

11. The method of claim 7, wherein:
wherein the user medical test data comprise free β-hCG measurements;
wherein the user free β-hCG measurements are expressed as a multiple of a gestation-specific median value;
wherein the step of comparing the user free β-hCG measurements against the one or more standards comprises comparing the distribution of the user free β-hCG measurements against free β-hCG measurements, expressed as multiples of a gestation-specific median value, representing average free β-hCG measurements for a statistically significant population, and determining the percentage deviation therefrom represented by the user's free β-hCG measurements; and
wherein the step of generating a variability-value comprises determining the likelihood ratio over a predefined operating range for the average free β-hCG measurements, determining the likelihood ratio, over the predefined operating range, for the user free β-hCG measurements, and identifying the maximum deviation, expressed as an absolute value, of the likelihood ratio for the user free β-hCG measurements from the likelihood ratio for the average free β-hCG measurements.

12. The method of claim 11, further comprising the step of correcting the user medical test data by the extent of deviation from the one or more standards determined for the user medical test data.

13. A method for quantifying the extent of human-introduced variability in medical test data relative to one or more standards for comparable medical tests, the method comprising the following steps:
provided user medical test data stored in a computer-readable storage medium;
comparing the user medical test data against one or more standards for comparable medical tests and determining the extent of deviation of the user medical test data from the one or more standards; and
generating a variability-value corresponding to the maximum absolute percentage deviation of the user medical test data from the one or more standards over a predefined operating range of values for the one or more standards;
wherein the user medical test data comprise free β-hCG measurements;
wherein the user free β-hCG measurements are expressed as a multiple of a gestation-specific median value;
wherein the step of comparing the user free β-hCG measurements against the one or more standards comprises comparing the distribution of the user free β-hCG measurements against free β-hCG measurements, expressed as multiples of a gestation-specific median value, representing average free β-hCG measurements for a statistically significant population, and determining the percentage deviation therefrom represented by the user's free β-hCG measurements; and
wherein the step of generating a variability-value comprises determining the likelihood ratio over a predefined operating range for the average free β-hCG measurements, determining the likelihood ratio, over the predefined operating range, for the user free β-hCG measurements, and identifying the maximum deviation, expressed as an absolute value, of the likelihood ratio for the user free β-hCG measurements from the likelihood ratio for the average free β-hCG measurements.

14. The method of claim 13, further comprising the step of correcting the user medical test data by the extent of deviation from the one or more standards determined for the user medical test data.

15. The method of claim 13, wherein:
the user medical test data further comprise fetal nuchal translucency measurements;
the user fetal nuchal translucency measurements are expressed as a multiple of a gestation-specific median value;
the step of comparing the user fetal nuchal translucency measurements against the one or more standards comprises comparing the distribution of the user fetal nuchal translucency measurements against fetal nuchal translucency measurements, expressed as multiples of a gestation-specific median value, representing average fetal nuchal translucency measurements for a statistically significant population, and determining the percentage deviation therefrom represented by the user fetal nuchal translucency measurements; and
the step of generating a variability-value comprises determining the likelihood ratio over a predefined operating range for the average fetal nuchal translucency measurements, determining the likelihood ratio, over the predefined operating range, for the user fetal nuchal translucency measurements, and identifying the maximum deviation, expressed as an absolute value, of the likelihood ratio for the user fetal nuchal translucency measurements from the likelihood ratio for the average fetal nuchal translucency measurements.

16. The method of claim 15, further comprising the step of correcting the user medical test data by the extent of deviation from the one or more standards determined for the user medical test data.

17. The method of claim 13, wherein:
wherein the user medical test data comprise maternal serum PAPP-A measurements;
wherein the user maternal serum PAPP-A measurements are expressed as a multiple of a gestation-specific median value;
wherein the step of comparing the user maternal serum PAPP-A measurements against the one or more standards comprises comparing the distribution of the user maternal serum PAPP-A measurements against maternal serum PAPP-A measurements, expressed as multiples of a gestation-specific median value, representing average maternal serum PAPP-A measurements for a statistically significant population, and determining the percentage deviation therefrom represented by the user's maternal serum PAPP-A measurements; and
wherein the step of generating a variability-value comprises determining the likelihood ratio over a predefined operating range for the average maternal serum PAPP-A measurements, determining the likelihood ratio, over the predefined operating range, for the user maternal serum PAPP-A measurements, and identifying the maximum deviation, expressed as an absolute value, of the likelihood ratio for the user's maternal serum PAPP-A measurements from the likelihood ratio for the average maternal serum PAPP-A measurements.

18. The method of claim 17, further comprising the step of correcting the user medical test data by the extent of deviation from the one or more standards determined for the user medical test data.

19. The method of claim 1, wherein:
the user medical data comprises medical test data submitted by one or more subscribers;
the step of generating a variability-value comprises generating a subscriber specific variability-value corresponding to the maximum absolute percentage deviation of the subscriber's medical test data from the one or more standards over a predefined operating range of values for the one or more standards; and
further comprising the step of providing the subscriber-specific variability-value to at least the subscriber.

20. The method of claim 19, further comprising the step of correcting each subscriber's medical test data by the extent of deviation from the one or more standards determined for the subscriber's medical test data.

21. The method of claim 19, wherein the one or more standards are based upon the average medical test results derived from the at least one computer-readable storage medium for storing the medical test data submitted by the one or more subscribers.

22. The method of claim 7, wherein:
the user medical data comprises medical test data submitted by one or more subscribers;
the step of generating a variability-value comprises generating a subscriber specific variability-value corresponding to the maximum absolute percentage deviation of the subscriber's medical test data from the one or more standards over a predefined operating range of values for the one or more standards; and
further comprising the step of providing the subscriber-specific variability-value to at least the subscriber.

23. The method of claim 22, further comprising the step of correcting each subscriber's medical test data by the extent of deviation from the one or more standards determined for the subscriber's medical test data.

24. The method of claim 22, wherein the one or more standards are based upon the average medical test results derived from the at least one computer-readable storage medium for storing the medical test data submitted by the one or more subscribers.

25. The method of claim 13, wherein:

the user medical data comprises medical test data submitted by one or more subscribers;

the step of generating a variability-value comprises generating a subscriber specific variability-value corresponding to the maximum absolute percentage deviation of the subscriber's medical test data from the one or more standards over a predefined operating range of values for the one or more standards; and further comprising the step of providing the subscriber-specific variability-value to at least the subscriber.

26. The method of claim 25, further comprising the step of correcting each subscriber's medical test data by the extent of deviation from the one or more standards determined for the subscriber's medical test data.

27. The method of claim 25, wherein the one or more standards are based upon the average medical test results derived from the at least one computer-readable storage medium for storing the medical test data submitted by the one or more subscribers.

* * * * *